US009381368B2

(12) United States Patent
Ranpura et al.

(10) Patent No.: US 9,381,368 B2
(45) Date of Patent: Jul. 5, 2016

(54) LEAD CONNECTOR ASSEMBLY FOR AN IMPLANTABLE MEDICAL DEVICE AND METHOD OF CONSTRUCTION

(71) Applicant: Boston Scientific Neuromodulation Corporation, Valencia, CA (US)

(72) Inventors: Himanshu Ranpura, Stevenson Ranch, CA (US); Jose Ulloa, Valencia, CA (US); Sean Walsh, Co. Clare (IE); James English, Co. Tipperary (IE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/612,178

(22) Filed: Feb. 2, 2015

(65) Prior Publication Data

US 2015/0251011 A1 Sep. 10, 2015

Related U.S. Application Data

(60) Provisional application No. 61/948,483, filed on Mar. 5, 2014, provisional application No. 62/021,932, filed on Jul. 8, 2014.

(51) Int. Cl.
*A61N 1/00* (2006.01)
*A61N 1/375* (2006.01)
*A61N 1/05* (2006.01)

(52) U.S. Cl.
CPC ............... *A61N 1/3754* (2013.01); *A61N 1/05* (2013.01); *A61N 1/3752* (2013.01)

(58) Field of Classification Search
CPC ..... A61N 1/05; A61N 1/3754; A61N 1/3752; H01R 23/00; H01R 2201/12
See application file for complete search history.

(56) References Cited

U.S. PATENT DOCUMENTS

| 6,516,227 B1 | 2/2003 | Meadows |
| 8,096,838 B2 | 1/2012 | Dilmaghanian |
| 8,190,259 B1 | 5/2012 | Smith et al. |

(Continued)

FOREIGN PATENT DOCUMENTS

| EP | 2517756 A1 | 10/2012 |
| WO | 2008/088568 A1 | 7/2008 |

OTHER PUBLICATIONS

U.S. Appl. No. 61/874,194, filed Sep. 5, 2013.

(Continued)

*Primary Examiner* — Scott Getzow
(74) *Attorney, Agent, or Firm* — Lewis, Reese & Nesmith, PLLC (57) ABSTRACT

A lead connector assembly for an Implantable Medical Device (IMD) is disclosed. The lead connector assembly includes a rigid elongated connector core having a core opening along its long axis. An alternating series of elastomer seals and header contacts are inserted into the core opening along the long axis and meet with an end stop to hermetically self-align the header contacts with contact openings along the sides of the core. A connector block can be inserted into an opening in the connector core, and sealed with an adhesive. Once the connector core, header contacts, seals, and connector block are subassembled, the connector core subassembly may be hermetically tested, and thereafter affixed to other subassemblies by affixing means on the connector cores. Feedthrough pins can then be connected to the header contacts through the contact openings, and overmolded with a header to the IPG's case.

31 Claims, 10 Drawing Sheets

(56) References Cited

U.S. PATENT DOCUMENTS

| | | |
|---|---|---|
| 8,224,450 B2 | 7/2012 | Brase |
| 8,523,617 B2 | 9/2013 | Seeley et al. |
| 2008/0274651 A1 | 11/2008 | Boyd et al. |
| 2009/0264943 A1 | 10/2009 | Barker |
| 2012/0053646 A1 | 3/2012 | Brase et al. |
| 2012/0185019 A1 | 7/2012 | Schramm et al. |

OTHER PUBLICATIONS

International Search Report and Written Opinion regarding corresponding PCT Application No. PCT/US2015/015043, dated Apr. 15, 2015.

LEAD CONNECTOR ASSEMBLY FOR AN IMPLANTABLE MEDICAL DEVICE AND METHOD OF CONSTRUCTION

CROSS-REFERENCE TO RELATED APPLICATIONS

This is a non-provisional application based on U.S. Provisional Patent Application Ser. Nos. 62/021,932, filed Jul. 8, 2014, and 61/948,483, filed Mar. 5, 2014, to which priority are claimed, and which are incorporated herein by reference in their entireties.

FIELD OF THE INVENTION

The present invention relates to implantable medical devices, and more particularly to an improved design and method of construction of a lead connector assembly for an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

Figure 1:
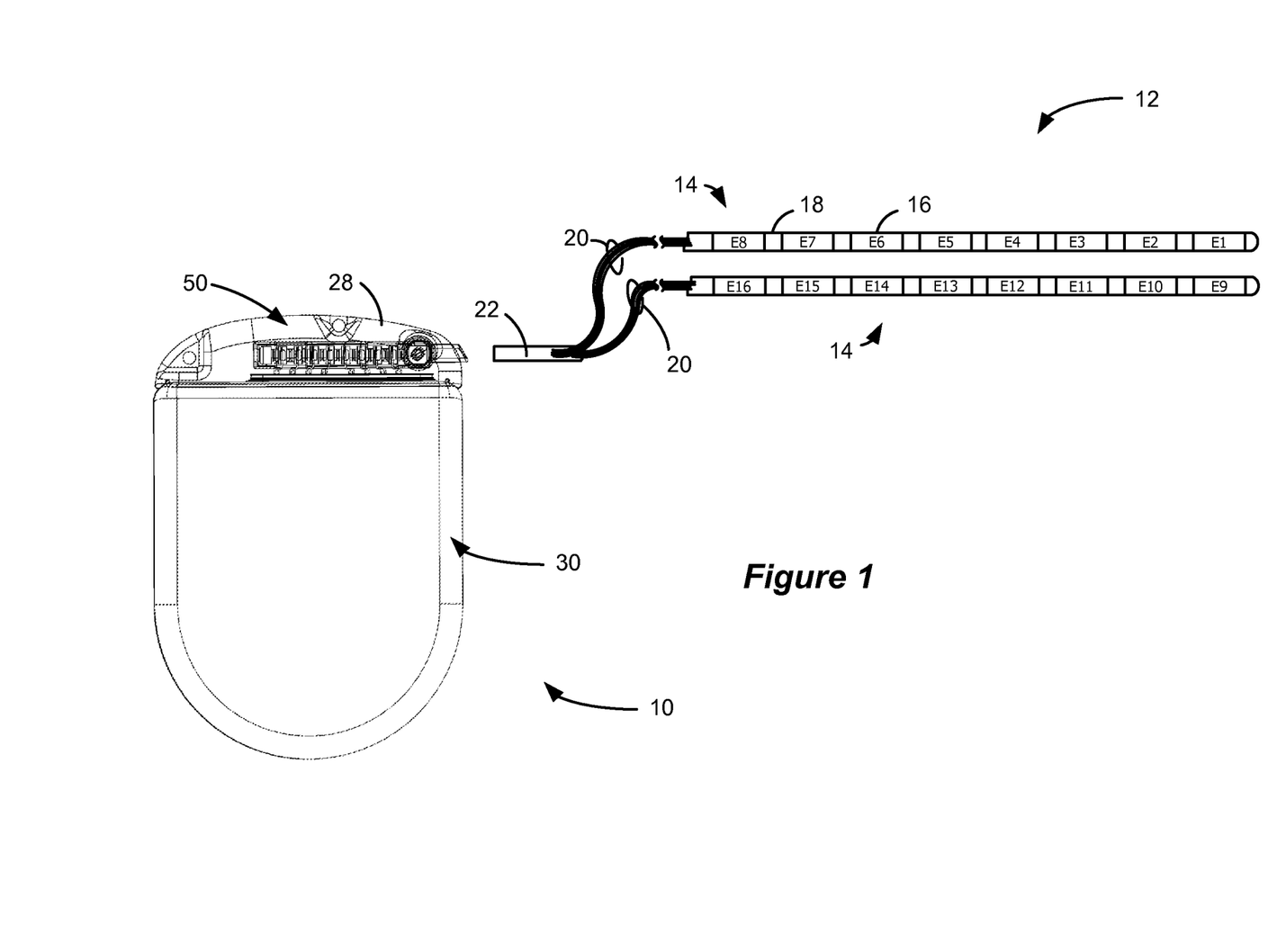
FIG. 1 shows an Implantable Pulse Generator (IPG) and the manner in which electrode leads are affixed to the IPG in accordance with the prior art.

An SCS system typically includes an Implantable Pulse Generator (IPG), whose structure and construction is further described in U.S. Provisional Patent Application No. 61/874,194, entitled "Construction for an Implantable Medical Device Employing an Internal Support Structure," filed Sep. 5, 2013 ("the '194 Application"), which is incorporated herein by reference in its entirety. The IPG 10 of the '194 Application is shown in FIG. 1, which includes a biocompatible device case 30 that holds the circuitry and battery 34 (FIG. 2) necessary for the IPG to function. The IPG 10 is coupled to electrodes 16 via one or more electrode leads 14 that form an electrode array 12. The electrodes 16 are carried on a flexible body 18, which also houses the individual signal wires 20 coupled to each electrode 16. The signal wires 20 are also coupled to proximal contacts 22, which are insertable into a lead connector assembly 50 fixed in a header 28 on the IPG 10, which header can comprise an epoxy for example. Once inserted, the proximal contacts 22 connect to header contacts 58 in the lead connector assembly 50, which header contacts 58 are in turn coupled by feedthrough pins 48 (not shown) to circuitry within the case 30, as will be explained subsequently. In the illustrated embodiment, there are sixteen electrodes 16 (E1-E16) split between two leads 14, although the number of leads and electrodes is application specific and therefore can vary. In a SCS application, electrode leads 14 are typically implanted on the right and left side of the dura within the patient's spinal cord. The proximal contacts 22 of the leads 14 are then tunneled through the patient's tissue to a distant location, such as the buttocks, where the IPG case 30 is implanted, at which point they are coupled to the lead connector assembly 50 in the header 28.

Figure 2:
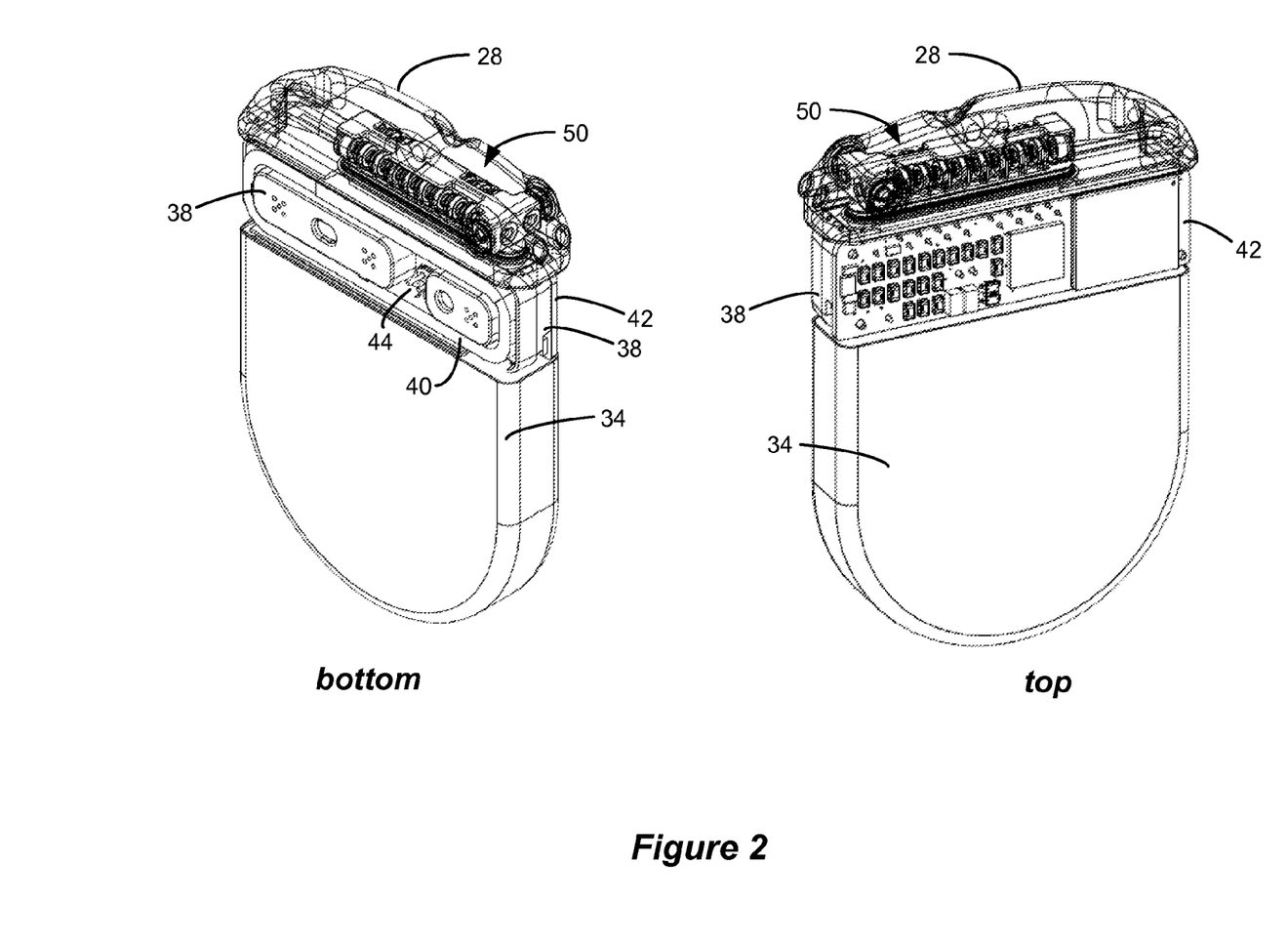
FIG. 2 shows bottom and top views of the IPG with its case removed in accordance with the prior art.

FIG. 2 shows perspective bottom and top sides of the IPG 10 with the case 30 removed so that internal components can be seen. In particular, a battery 34, communication coil 40, and a printed circuit board (PCB) 42, can be seen. As explained in the '194 Application, these components are affixed to and integrated using a rigid (e.g., plastic) support structure 38. Battery 34 in this example is a permanent, non-wirelessly-rechargeable battery. (Battery 34 could also be rechargeable, in which case either coil 40 or another recharging coil would be used to wirelessly receive a charging field that is rectified to charge the battery 34). The communication coil 40 enables communication between the IPG 10 and a device external to the patient (not shown), thus allowing bidirectional communication to occur by magnetic induction.

The ends of coil 40 are soldered to coil pins 44 molded into the support structure 38 to facilitate the coil 40's eventual connection to circuitry on the IPG PCB 42. IPG PCB 42 integrates the various circuits and electronics needed for operation of the IPG 10. As shown in FIG. 2, coil 40 is proximate to the bottom side of the support structure 38 and case 30, while the IPG PCB 42 is proximate to the top side.

Figure 3A:
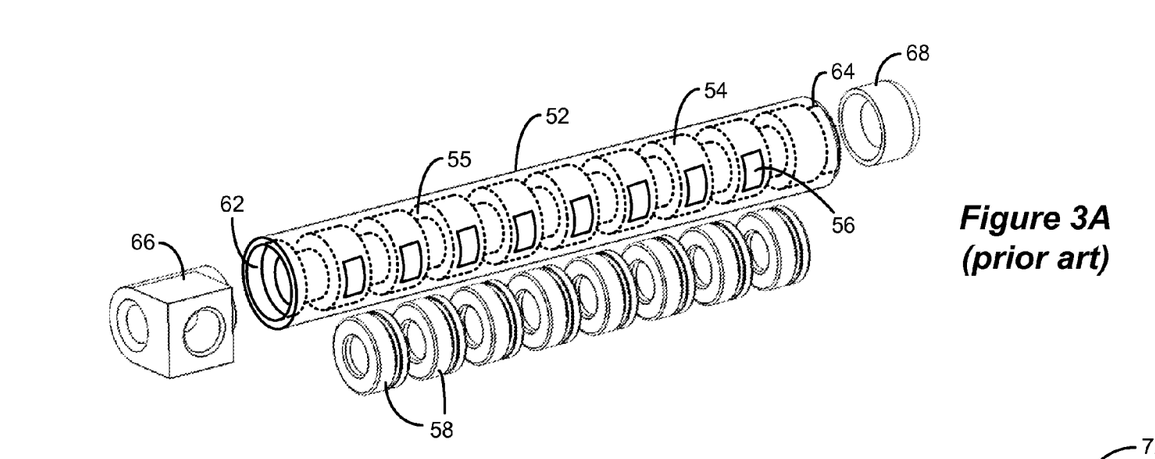
FIGS. 3A-3D show steps for constructing a lead connector assembly for the IPG in accordance with the prior art.

Construction of the lead connector assembly 50 is shown starting with FIG. 3A. Construction begins with an elastomer connector seal 52 formed of silicone for example. As can be seen, the connector seal 52 has been molded to include contact recesses 54 separated by narrower-diameter separator portions 55 formed of the connector seal 52 material. The contact recesses 54 are accessible through slits 56 in the side of the connector seal 52. During construction, header contacts 58, which are largely donut-shaped and formed of a rigid conductive material, are pressed through the slits 56, and come to rest inside of the seal 52 in the contact recesses 54. Once inserted, the header contacts 58 are captured firmly, and are electrically isolated from each other by the separator portions 55 of the connector seal 52. In the example shown, the connector seal 52 includes eight header contacts 58, which eventually will couple to the eight proximal contacts 22 on one of the leads 14 (FIG. 1).

Once all header contacts 58 have been positioned in the seal 52, adhesive is applied to opening 62 at one end of the seal 52, and a connector block 66 is inserted into the opening 62 and adhered to the connector seal 52. A medical grade adhesive suitable for this task includes Silastic® medical adhesive manufactured by Dow Corning Corporation or other adhesives provided by NuSil Silicone Technology LLC. Curing of such adhesives can take up to 12 hours. A platinum end cap 68 is also inserted into the opening 64 at the other end of the seal 52. After inserting the end cap 68 and adhesive curing of the connector block 66 to the seal 52, the resulting connector seal subassembly 70 is shown in FIG. 3B.

Figure 3B:
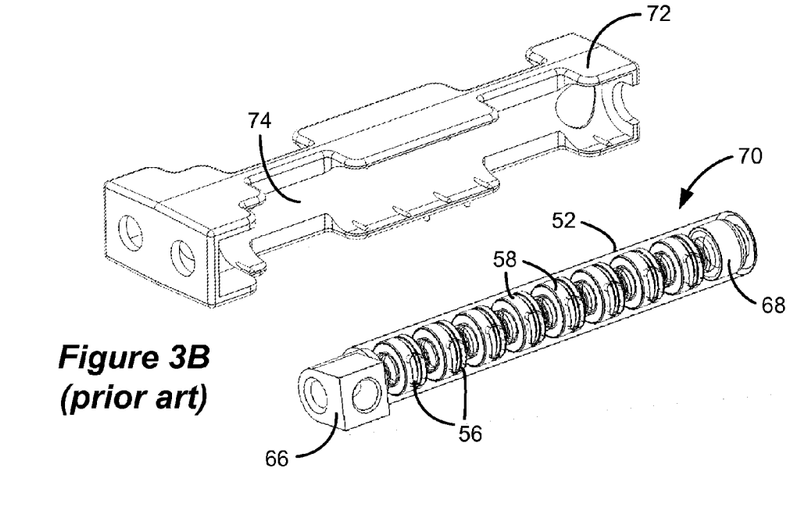
Figure 3C:
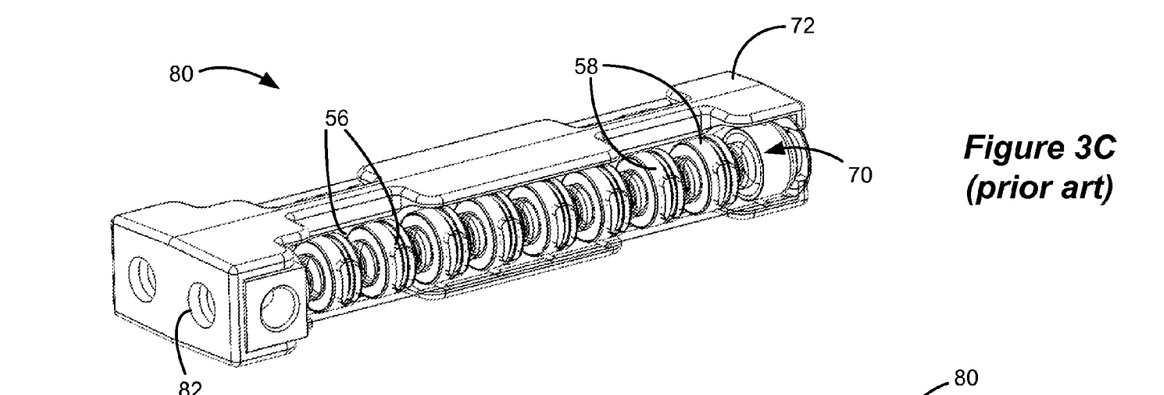

Continuing with FIG. 3B, connector seal subassembly 70 is then affixed within a recess 74 in a carrier 72, which may be formed of a rigid plastic such as polyurethane. As shown, the carrier 72 can accompany two connector seal subassemblies 70 on both of its sides to support an IPG 10 with sixteen electrodes 16 in this example. The connector seal subassembly(ies) 70 can be affixed and cured within the carrier 72 using an adhesive such as those just mentioned. Adhesive can be applied to the areas of the carrier that will be adjacent to the connector block 66 and the end cap 68 to ensure a secure placement. The resulting carrier subassembly 80 is shown in FIG. 3C.

Figure 3D:
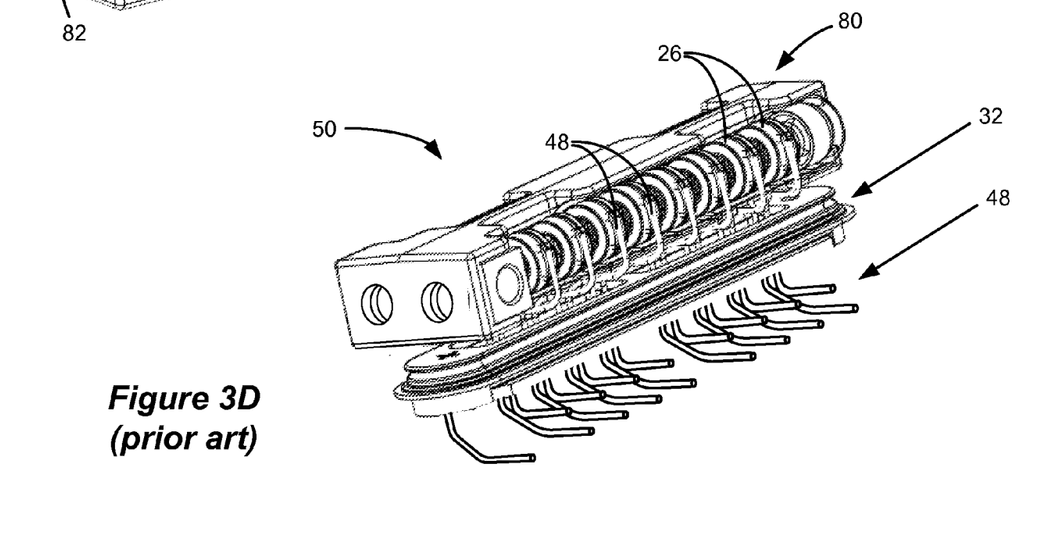

After the carrier subassembly 80 has been completed, it is mechanically and electrically connected to a feedthrough 32 and feedthrough pins 48 to complete the lead connector assembly 50, as shown in FIG. 3D. To do this first, feedthrough pins 48 are slipped through the feedthrough 32, and then insulation tubes (not shown) are put on each of the feedthrough pins 48 to cover a portion of the feedthrough pins 48 between the feedthrough 32 and the slits 56. The insulation tubes are shorter than the feedthrough pins 48, thus allowing some portion of first ends of each feedthrough pin 48 to remain exposed for connection to the contacts 58. Adhesive is then placed on each feedthrough pin 48 to adhere the insulation tubes to the pins, and then the uncovered first ends of the pins 48 are soldered to the header contacts 58 through the slits 56 in the connector seal 52. After soldering, the silts 56 containing the soldered connections are then covered with adhesive and cured as before to create a hermetic seal.

The now completed lead connector assembly 50 can then be coupled to the remainder of the IPG circuitry, as discussed in detail in the above-incorporated '194 Application. Such remaining IPG construction steps are not discussed here in detail, but involve soldering the second ends of the feedthrough pins 48 to the PCB 42; affixing the IPG circuitry in the case 30; welding the case 30 together and to the feedthrough 32; and molding the header 28 over the lead connector assembly 50 and to the case 30.

The inventors see that this process for forming the lead connector assembly 50 for the IPG 10 can be improved upon. For one, the process at several places requires the use of adhesive: to adhere the connector block 66 and end cap 68 to the connector seal 52 (FIG. 3B); to affix the connector seal subassembly 70 inside of the carrier 72 (FIG. 3C); to seal the insulation tubes to the feedthrough pins 48; and to cover the slits 56 in the connector seal 52 once the header contacts 58 have been soldered to the feedthrough pins 48 (FIG. 3D). This slows down manufacture of the lead connector assembly 50, in particular because the adhesive must be cured at each stage before subsequent construction steps can begin. Additionally, certain of the components, such as the end cap 68, are costly.

Moreover, there is no good means for testing the lead connector assembly 50, or its constituent subassembly(ies) 70 or 80, with respect to hermeticity—i.e., with respect to how effectively their construction has rendered them impervious to moisture and/or epoxy ingress.

This is unfortunate, as it means that assembly 50 or subassembly 70 or 80 could have a hermeticity concern that would not be noticeable during IPG manufacturing. This wastes manufacturing resources, as a defective lead connector assembly 50 may be coupled to otherwise functioning IPG circuitry, and worse can affect IPG reliability after implantation into a patient. An improved lead connector assembly remedying these concerns is thus sought, and is disclosed by the inventors.

DETAILED DESCRIPTION

An improved lead connector assembly for an Implantable Medical Device (IMD) such as an Implantable Pulse Generator (IPG) is disclosed as is its method of manufacture. The lead connector assembly includes one or more rigid elongated connector cores each having a core opening along its long axis. An alternating series of elastomer seals and header contacts are inserted into the core opening along the long axis where they are interference fit within the opening and meet with an end stop to hermetically self-align the header contacts with contact openings along the sides of the core perpendicular to the long axis. A connector block can then be inserted into an opening in the connector core that is also radially perpendicular to the long axis. An adhesive can be used to seal the connector block into the connector core, but no adhesive is necessary to secure the header contacts or the seals. Once the connector core, header contacts, seals, and connector block are subassembled, connector core subassemblies may then be hermetically tested as necessary, and thereafter affixed to each other by affixing means. Feedthrough pins can then be connected to the header contacts through the contact openings, and overmolded with a header to the IPG's case.

Figure 8:
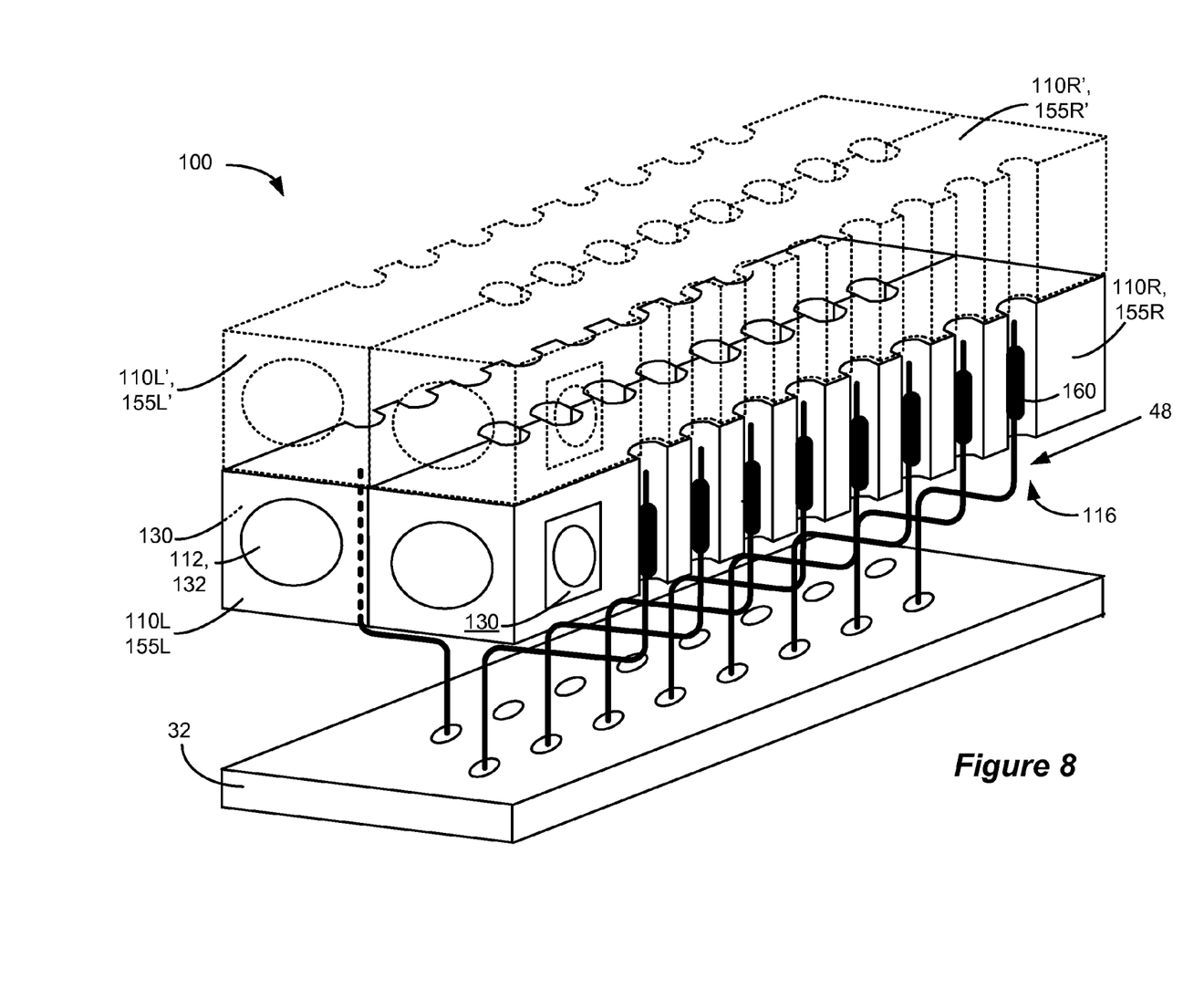
FIG. 8 shows connection of feedthrough pins to the header contacts in connected connector core subassemblies according to an embodiment of the invention.

The improved lead connector assembly 100 is shown fully constructed in FIG. 8, as connected to the feedthrough pins 48 and the feedthrough 32, and which is ready for connection to the remainder of the circuitry in an IPG, as discussed for example in the above-incorporated '194 Application. As shown, construction of the lead connector assembly 100 centers around the use of connector cores 110.

Figure 4A:
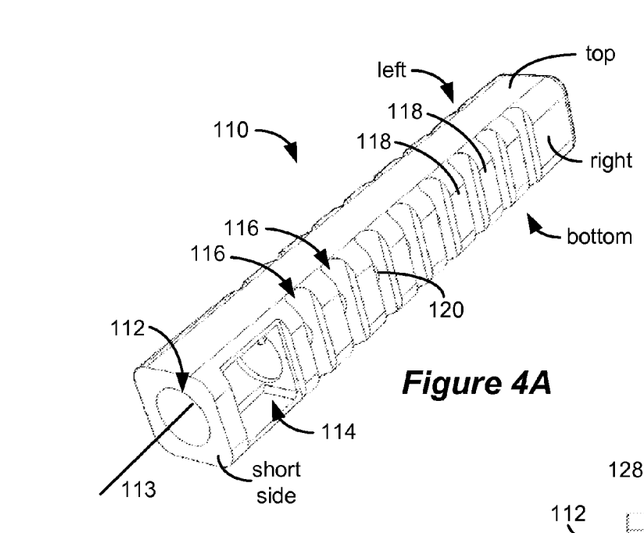
FIGS. 4A-4E show different views of a connector core used in the improved lead connector assembly according to an embodiment of the invention.
Figure 4B:
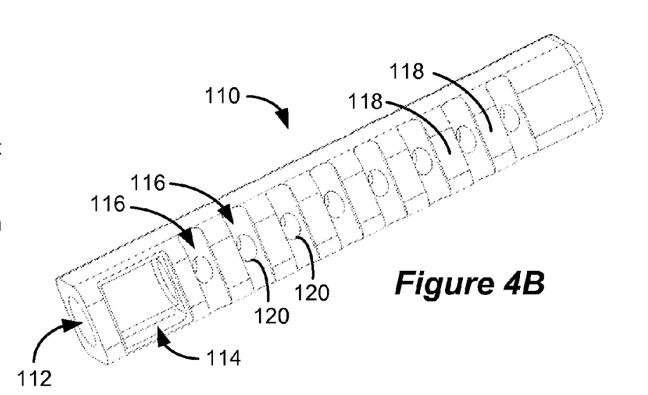
Figure 4C:
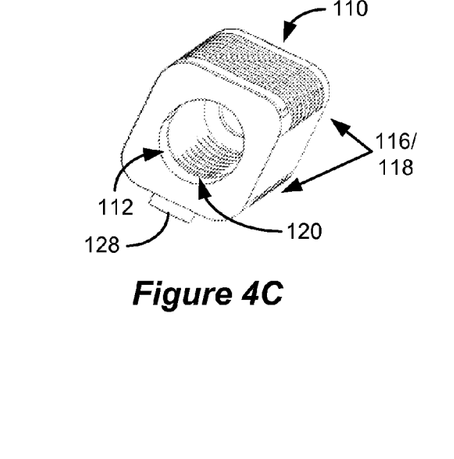
Figure 4D:
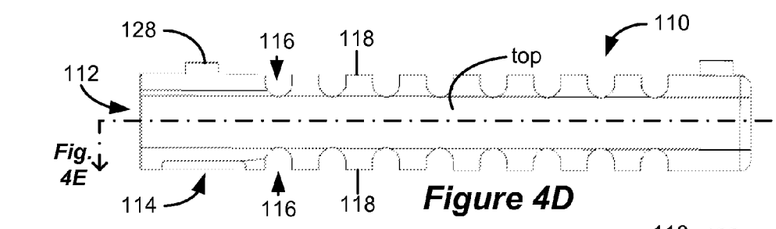
Figure 4E:
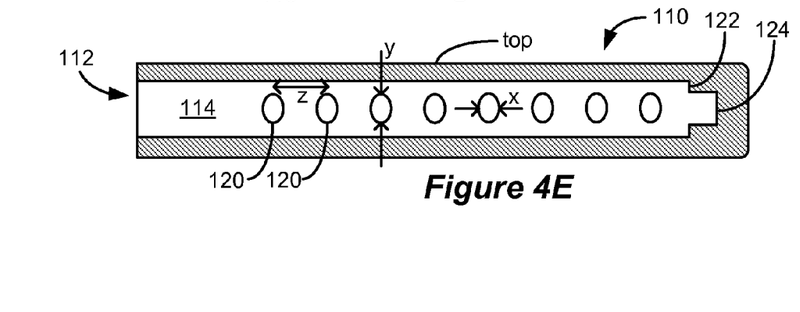

FIGS. 4A-4E show various view of a connector core 110, including various perspective view (FIGS. 4A-4C), a top down view (FIG. 4D), and a cross-sectional view (FIG. 4E). Unlike the connector seal 52 of the prior art, the connector core 110 is formed of rigid insulative plastic, preferably of a medical grade Thermoplast Polyurethane (TPU) such as Isoplast®, provided by Lubrizol Corporation. Other hard plastics such as Tecothane® TPU could also be used, but Isoplast is believed advantageous as its material properties are similar to those of epoxy in terms of rheology and dimensional stability, and because it has better dimensional stability.

As shown, the elongated connector core 110 comprises major faces defining a three-dimensional rectangle, with square short sides perpendicular to a long axis 113, left and right sides, a top, and a bottom. (The left, right, top and bottom major faces can generally be referred to as long sides). One of the short sides includes a core opening 112 which proceeds along the long axis 113 of the connector core 110, but which does not proceed through the other short side, but instead reaches one or more end stops 122 and 124 formed in the material of the connector core 110, as best shown in the cross section of FIG. 4E, and as explained further below. Note that the design of the connector core 110 doesn't require an expensive platinum end cap (compare 68; FIG. 3A).

In communication with the core opening 112 is a connector block opening 114 which appears on one of the left or rights sides of the connector core 110 (right side as shown) and perpendicular to the long axis 113. Also present on each of the left and right sides are recesses 116 containing contact openings 120 in communication with the core opening 112 which are also perpendicular to the long axis 113. Between each of the recesses 116 are non-recessed portions 118 comprising the major faces of the left and right sides. The connector core 110 is preferably molded to include these various features, but could also be milled from a solid block in other examples.

Figure 5:
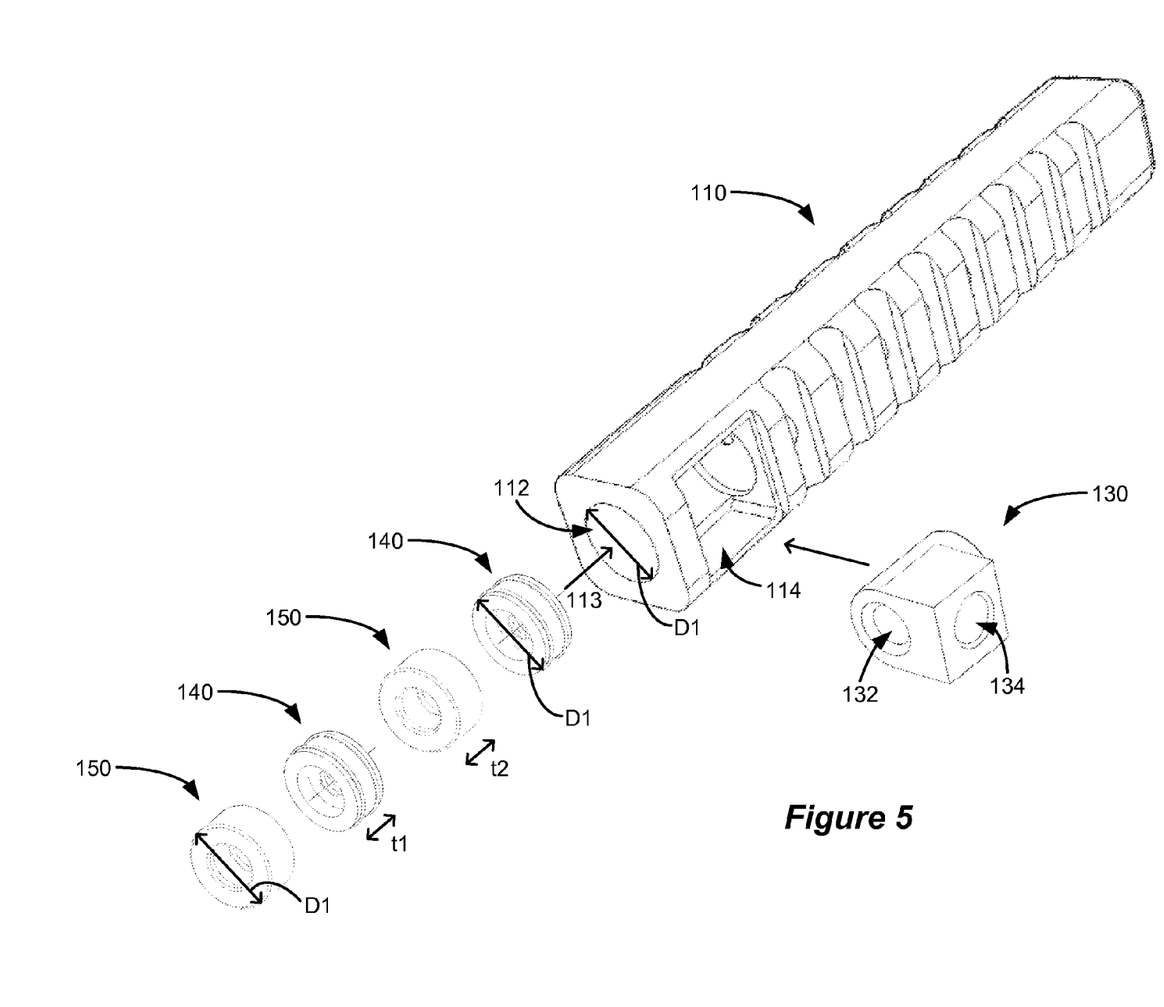
FIGS. 5, 6A, and 6B show steps for including header contacts, seals, and a connector block into the connector core to form a connector core subassembly according to an embodiment of the invention.

During construction, the connector core 110 is filled through core opening 112 with a series of header contacts 150 and seal 140, as shown in FIG. 5. The seal 140 may be formed of an elastomer material such as silicone for example, while the header contacts 150 comprise a rigid conductive body 150a containing a deformable inner conductive spring 150b, as shown in cross section in FIG. 6B. An alternating series of seals 140 and header contacts 150 are placed on a ramming tool (not shown) and are forced into the opening 112 along its long axis 113 until they are touching and are pushed against an end stop 122 near the other short side. The diameters of the core opening 112, the seals 140, and the header contacts 150 (all roughly D1) are sized so that the seal 140 and header contacts 150 are held in the core opening 112 by an interference fit.

Figure 6A:
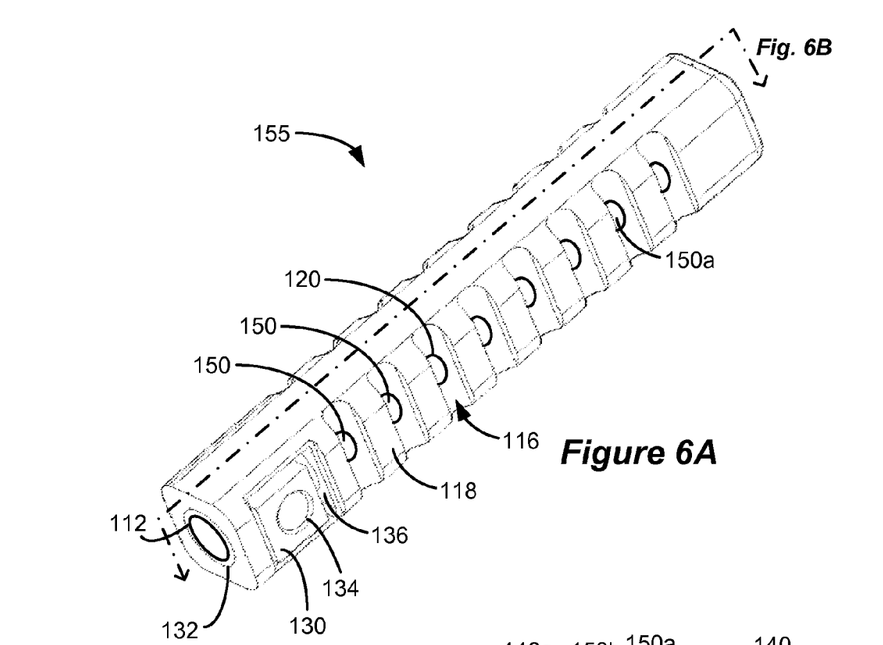
Figure 6B:
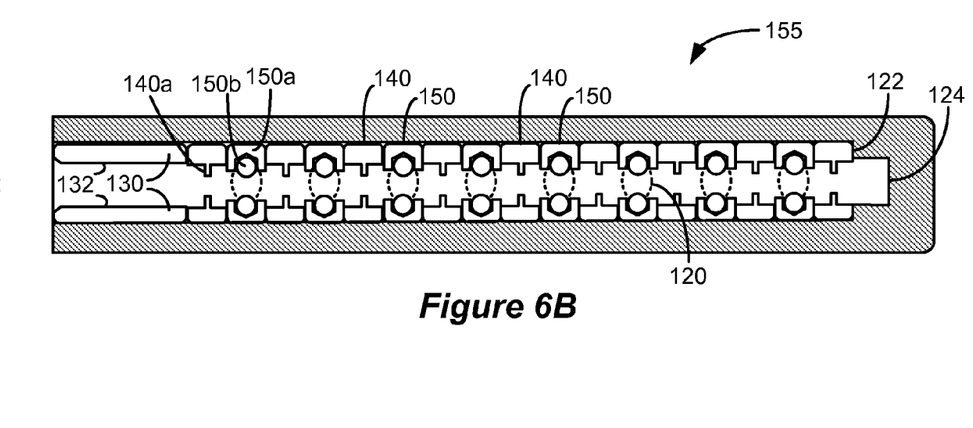

The end stop 122 is positioned in the connector opening 122 such that, in conjunction with the thickness of the seals 140 (t1) and the header contacts 150 (t2), the header contacts 150 are self-aligned with the contact openings 120 in the recesses 116 in the connector core 110, again as best shown in FIG. 6B. In this regard, it is beneficial to set the contact openings 120 at distances z (FIG. 4E) equal to the sum of thicknesses t1 and t2. More particularly, the conductive body 150a of the header contacts 150 will now be accessible through the contact openings 120, as shown in FIG. 6A. Note that the interference fit between the body 150a of the header contacts 150 and the contact openings 120 provides a hermetic seal to prevent the ingress of fluid into the interior of the connector core 110.

Note also that the thickness (t2) and diameter (D1) of the header contacts 150 is larger than corresponding dimensions x and y (FIG. 4E) of the contact openings 120, thus establishing a hermetic seal between the header contacts 150 and the edges of the contact openings 120 to prevent fluid ingress. Note that the rigid material of the connector core 110 will not significantly deform as would an elastomer seal (compare 52; FIG. 3A). Although the seals 140 and header contacts are shown as having roughly the same thickness t1 and t2, this is not strictly necessary, and the thickness can be different while at the same time self-aligning the header contacts 150 to the contact openings 120.

Although not strictly necessary, note that a seal 140 is preferably provided at the beginning and end of the alternating series of the seals 140 and header contacts 150, such that the there will be one extra seal 140 compared to the number of header contacts 150. Note that the seals 140 can include a smaller diameter flange 140a extending toward the connector core's long axis, as shown in FIG. 6B. Note that connector core 110 can be fabricated to accommodate any number of header contacts 150, whether even or odd, although in the example shown each connector core accommodates eight contacts, similar to the prior art example discussed earlier. While it is preferred for simplicity that all of the seals 140 have a uniform thickness (t1) and construction, this is not strictly necessary, particularly as concerns the first and last seals 140 in the series.

After inserting the seals 140 and header contacts 150, a connector block 130 is inserted into the connector block opening 114 on the side of the connector core 110, and the opening 114 and connector block 130 can be sized for a comfortable (if not interference) fit. The connector block 130 contains a receptacle 134 perpendicular to the long axis 113 for receiving a set screw (not shown) to lock the proximal end of the lead in place when inserted into the connector core 110. The connector block 130 further includes a lead opening 132 for receiving the proximal end of the lead 14 and passing it through the core opening (and through the centers of the seals 140 and header contacts 150) along the core's long axis 113. The diameter of the lead opening 132 may be slightly larger than the diameter (D2) of the proximal end of the lead 14, while the inner diameters of the flanges 140a in the seals 140 and the springs 150b in the header contacts 150 may be slightly smaller than the lead diameter. This allows the proximal end of the lead to be interference fit when inserted into the connector core 110, as the flanges 140a and springs 150b are compressible.

Note that the elastomer flanges 140a (with a diameter slightly smaller than the diameter D2 of the lead) provide good hermeticity to prevent fluid ingress through the lead opening 132 into the interior of the connector core 110, which fluid ingress could otherwise short the header contacts 150. The proximal end of the lead 14 can be pressed along the long axis 113 until its end reaches a lead end stop 124, which will cause the proximal contacts 22 on the lead 14 to naturally align in positions with the springs 150a in the header contacts 150. While separate ends stops 122 and 124 are shown for the seals 140/header contacts 150 and the lead 14 respectively, this is not strictly necessary and a single end stop could instead be used for both by appropriate sizing of the components.

Once the connector block 130 is inserted into the connector core 110, it is preferably affixed in place using an adhesive. In this regard, the area of connector block face containing the set screw receptacle 134 can be formed smaller than the area of the connector block opening 114 so as to form a gap 134 between the connector block 130 and the connector core 110 for receiving the adhesive. In a preferred example, the adhesive placed in gap 134 is curable with ultra-violet light, and can comprise Multi-Cure® 1128A-M serial medical device adhesive manufactured by Dymax Corporation. Using a UV-curable adhesive is preferred to speed manufacturing, although traditional, slower-curing adhesives such as those mentioned earlier could also be used. Note that the adhesive placed in gap 134 will flow between the outer surface of the connector block 130 and the inner surface of the connector block opening 114, thus providing good hermeticity and preventing fluid ingress into the interior of the connector core 110. At this point, a connector core subassembly 155 is complete.

Before discussing further steps in the construction of the lead connector assembly 100, an advantage of connector core subassembly 155 fabricated to this point is noted, specifically the fact that the connector core subassemblies 155 can be hermeticity tested prior to further IPG manufacture and incorporation of the subassembly into a lead connector assembly 100 (FIG. 8). For example, a seal plug (not shown) can be inserted into the lead opening 132 in each assembly 155, which can then be placed in a high pressure, high humidity autoclave for example. Whether a connector core subassembly 155 has been constructed with good hermeticity can be verified by determining whether there is any drop in pressure or whether fluid ingress can be visually verified through the preferably clear material of the connector core 110. The ability to hermeticity test the connector core subassemblies 155 is especially desirable in case a header contact 150 did not properly self-align with its contact opening 120 when the header contacts 150 and seals 140 were inserted as explained above, thus creating a hermeticity breach between the header contact 150 and an edge of its contact opening 120. However, as discussed above, proper dimensioning and spacing of the various components (x, y, z, t1, t2, D1, D2) are designed to minimize such hermeticity concerns.

Determining hermeticity of the connector core assemblies 155 at this point benefits IPG manufacturing and reliability, because faulty assemblies 155 can be discarded without putting the entire IPG at risk of failure. It should be noted that the components comprising the connector core subassemblies 155 are generally transparent (except the contacts 150 and the connector block 130), which can facilitate visual assessment of where subassembly 155 might have failed hermeticity testing.

Figure 7:
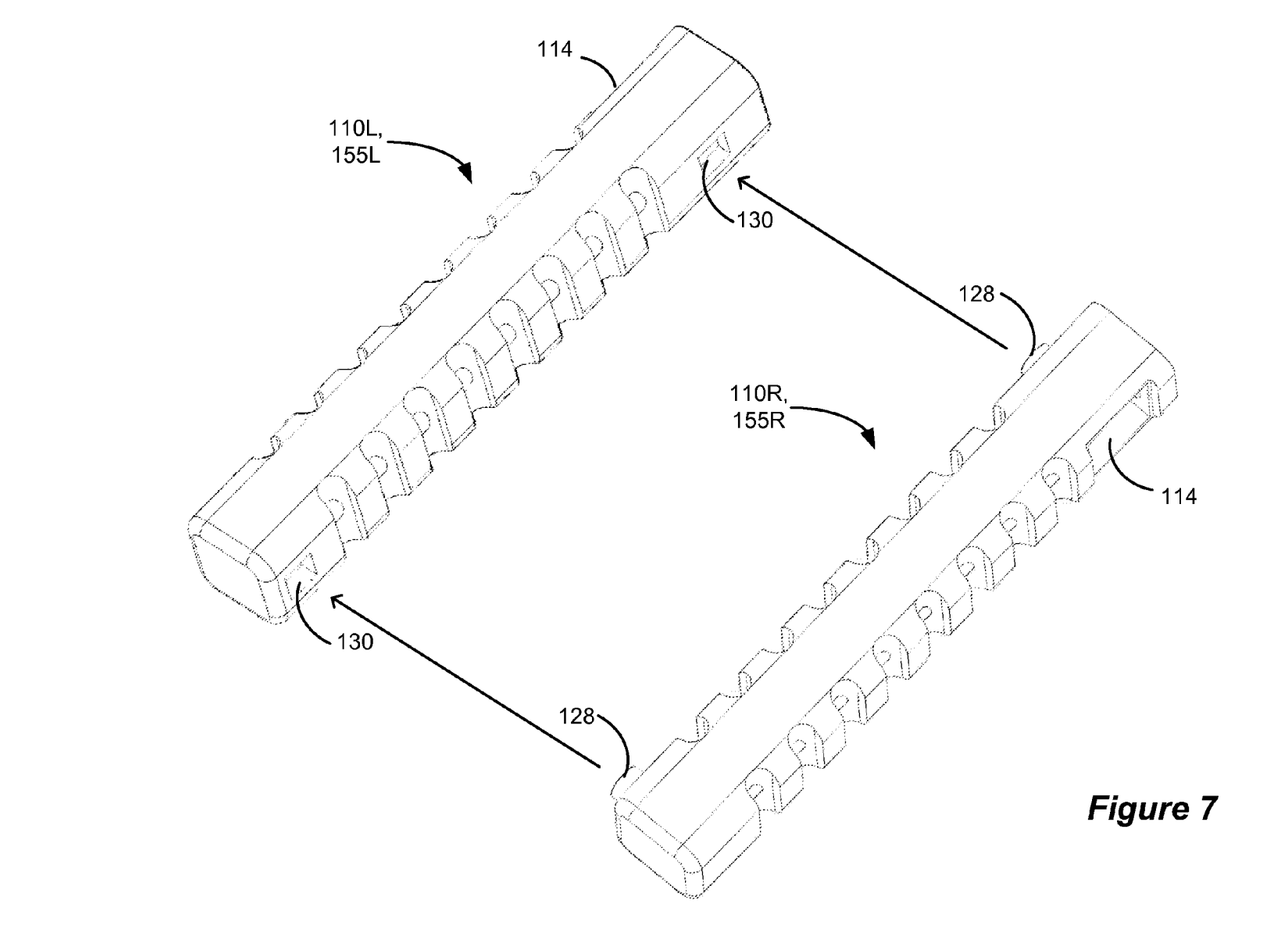
FIG. 7 shows how the connector core subassemblies can be connected together according to an embodiment of the invention.

The rigid nature of the connector core 110 material as well as its generally rectangular shape provide another benefit not provided by the prior art connector seal subassemblies 70, namely the ability to rigidly connect connector core subassemblies 155 together without the use of a separate carrier (compare 72, FIG. 3B). Thus, as shown in FIG. 7, the long sides of the connector cores 110 can include affixing means formed in or of the connector core 110 material for snapping the connector core subassemblies 155 to each other, such a male 128 and female 130 joints, which can affix by an interference fit similar to children's Lego® blocks.

In this regard, it can be beneficial to construct connector cores 110 with different shapes depending on where they will eventually be mounted inside the IPG's header. For example, FIG. 7 shows left and right connector cores 110L and 110R (resulting in left and right connector core subassemblies 155L and 155R), with affixing means formed on long sides that will face each other (and preferably touch) when they are connected. Thus, male joints 128 appear on the left side of 110/115R, and female joints 130 appear on the right side of 110/155L. Other affixing means formed in or of the connector core 110 material, such as snaps, clips, clasps, screws, hooks, slots, slits, etc., in matable forms can be molded as part of connector core 110 fabrication, or milled into the connector core 110 later. Although not shown, the top and bottom of the connector cores 110 could also contain similar affixing means to stack connector core subassemblies 155 on top of each other (as optionally shown in dotted lines in FIG. 8). Even if affixing means formed in or of the connector core 110 material are not provided, the generally flat long sides of the connector cores lend themselves to being easily connected by adhesives, by banding them together, by snaps, by clips, by clasps, by screws or by other affixing means. Although it is preferred to affix cores 110 to each other once completed as subassemblies 155, the cores 110 may also be affixed prior to inserting the seals 140, the header contacts 150, and the connector blocks 130 (FIG. 5).

Once the connector core subassemblies 155 are connected, they can be electrically coupled to the feedthrough pins 48 as shown in FIG. 8 to form the completed lead connector assembly 100, which also shows an idealized feedthrough 32 (see FIG. 3D for a more realistic view). Still further benefits are realized at this stage. For example, the recesses 116 are configured to receive ends of the feedthrough pins 48, which can generally rest in the recesses 116 in proximity to the contacts 150 accessible through the connector openings 120. The rigid nature of the connector cores 110, and in particular non-recessed portions 118, will protect the feedthrough pins 48 so received, which facilitates their welding. In this regard, resistive welding 160 can be used to electrically couple the feedthrough pins 48 to the contacts.

At this point, an adhesive can be placed over the welds 160 as occurred in the prior art, although this is not strictly necessary because, as described earlier, the interference fit between the contacts 150 and the contact openings 120 naturally provides for a hermetic seal. Instead, any additional hermeticity safeguards with respect to the lead connector assembly 100 are addressed when the header 28 is subsequently overmolded (not shown). Note that construction of the lead connector assembly 100 thus only uses a single adhesive step to connect the connector block 130 to the connector core 110, compared to several time- and labor-consuming that were needed for the prior art as discussed in the Background.

As shown in dotted lines, and as alluded to earlier, the design and construction of the connector cores 110 allows them to be easily stacked (see 110L/R' and 155L/R') to allow a larger number of IPG electrodes 16 to be supported (in this case thirty-two instead of sixteen). As also mentioned earlier, the connector cores 110 can have affixing means (see FIG. 7) on their tops and bottoms (not shown) to promote core connectability. Other numbers of connector cores 110 may also be used, including one, or even odd numbers of cores.

Modifications are possible. For example, while it is preferable to provide recesses 116 for the connector openings 120 and non-recessed portions 118 on both sides of the connector cores 110, this is not strictly necessary, as the feedthrough pins 48 may only connect to one side of the completed connector core subassemblies 155 (preferably the side also containing the connector block opening 114, as shown in FIG. 8). As such, the other side of the connector cores 110 can lack these features and be flat, although they may still optionally contain the affixing means 128 and 130 discussed earlier (FIG. 7).

Figure 9:
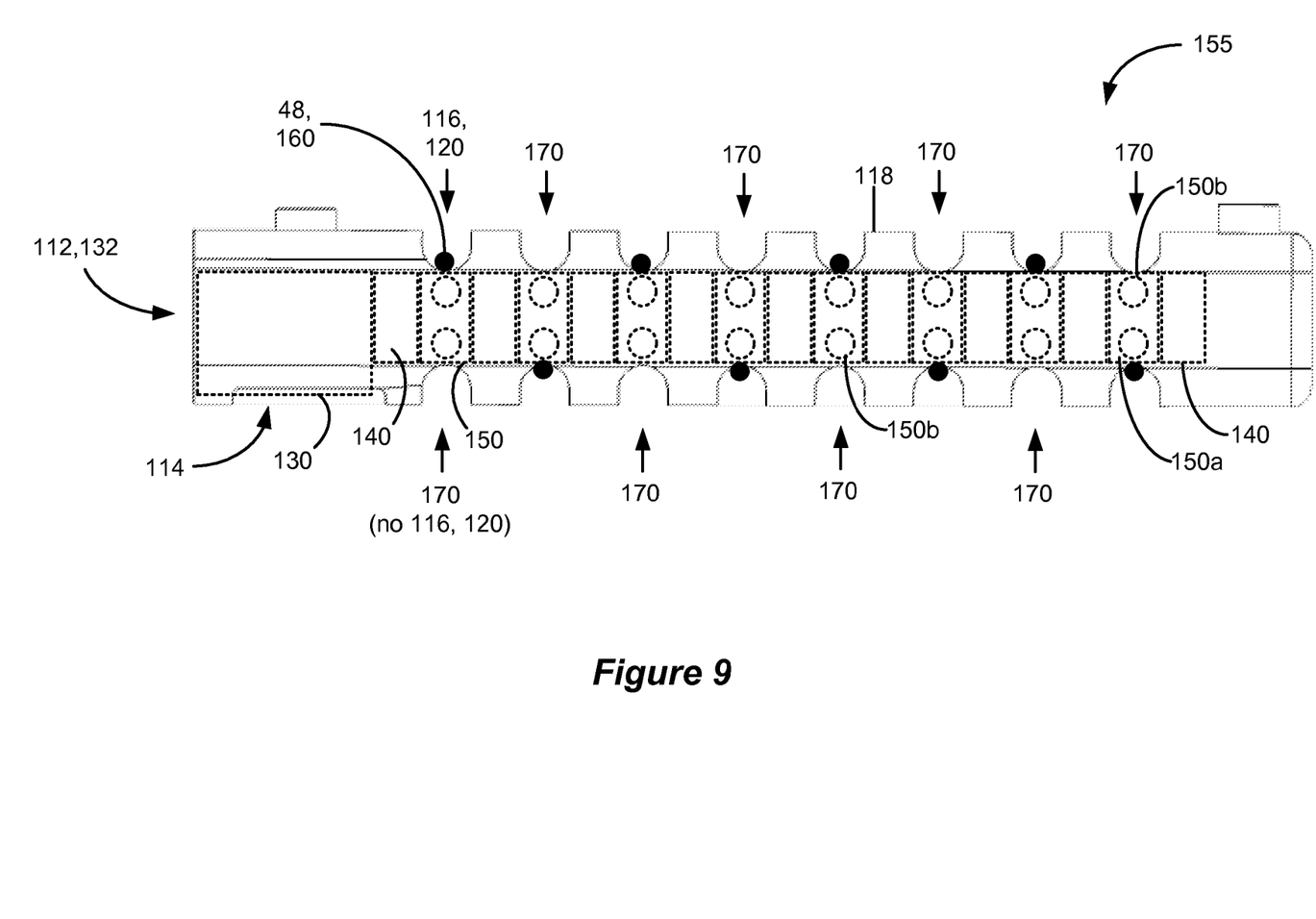
FIG. 9 shows connection of feedthrough pins to the header contacts on both sides of a connector core subassembly according to an embodiment of the invention.

Additionally, a connector core subassembly 155 can connect to feedthrough pins 48 on both of its sides, as shown in the top down view of FIG. 9. If the feedthrough pins 48 are straddled in their positions on both sides of the connector core subassembly 155 as shown, recesses 116 and contact openings 120 would not be needed on the opposite side of the connector core 110 (i.e., in location 170, although they are still shown), and so the recesses 116 and contact openings 120 could also be straddled on both sides. Recesses 116, connector openings 120, and non-recessed portions 118 could also occur on the tops and bottoms of the cores 110 (not shown) to allow coupling to the feedthrough pins 48 in those locations.

It should be noted that the above construction steps are merely examples of how the IPG 10 as designed can be constructed, and other manners are also possible. For example, construction steps can occur in different orders, or involve different sub-steps or the consolidation of steps.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A subassembly for an implantable medical device, comprising:
   a rigid insulative core having a long axis;
   a core opening along the long axis;
   an alternating series of contacts and seals in the core opening;

a plurality of contact openings in the core along and perpendicular to the long axis, wherein one of the contacts is accessible through each of the contact openings;

a connector block opening in the core and perpendicular to the long axis; and a connector block in the connector block opening having a lead opening configured to receive a proximal end of a medical lead and to pass the proximal end along the long axis through the core opening.

2. The subassembly of claim 1, wherein the core comprises major faces defining a three-dimensional rectangle, with short sides perpendicular to the long axis, and long sides parallel to the long axis.

3. The subassembly of claim 2, wherein at least one of the long sides includes affixing means for connecting the subassembly to another similarly-constructed subassembly.

4. The subassembly of claim 2, wherein the core opening proceeds through one of the short sides but not the other short side.

5. The subassembly of claim 4, wherein at least one of the long sides comprises the plurality of contact openings.

6. The subassembly of claim 5, wherein the at least one long side further comprises a plurality of recesses, wherein one of the plurality of contact openings appears in each of the recesses.

7. The subassembly of claim 6, wherein the recesses are configured to receive feedthrough pins to be welded to the contacts accessible through the contact openings in the recesses.

8. The subassembly of claim 1, wherein the connector block is affixed in the connector block opening by an adhesive.

9. The subassembly of claim 1, wherein the connector block further comprises a receptacle configured to receive a set screw, wherein the receptacle is perpendicular to the long axis.

10. The subassembly of claim 1, wherein the seals are formed of an elastomer material.

11. The subassembly of claim 1, wherein the contacts and seals are touching in the alternating series.

12. The subassembly of claim 11, wherein the contacts and seals are interference fit in the core opening.

13. The subassembly of claim 12, wherein the core opening ends along the long axis at an edge stop inside the core, and wherein the alternating series of contacts and seals in the core opening are pushed against the end stop.

14. The subassembly of claim 13, wherein the end stop is configured to self-align the contacts with the plurality of contact openings when the alternating series is pushed against the end stop.

15. The subassembly of claim 1, further comprising a plurality of feedthrough pins each electrically coupled to one of the contacts accessible through one of the connector openings.

16. The subassembly of claim 1, wherein a beginning and end of the alternative series comprise seals.

17. A lead connector assembly for an implantable medical device, comprising:

at least first and second cores formed of a rigid insulative material, each core having a long axis, each core comprising short sides perpendicular to its long axis, and long sides parallel to its long axis, wherein the first and second cores are positioned such that a first long side of the first core is facing a first long side of the second core, wherein the cores each comprise a core opening along its long axis;

an affixing means on its first long side connected to the first side of the other core;

a plurality of contact openings along and perpendicular to its long axis; and a connector block having a lead opening configured to receive a proximal end of a medical lead and to pass the proximal end along its long axis through its core opening.

18. The assembly of claim 17, wherein the first and second cores are touching at their first sides.

19. The assembly of claim 17, wherein the core openings proceed through one of the short sides of each of the cores but not the other short side of each of the cores.

20. The assembly of claim 19, wherein at least second sides opposite the first sides on each of the cores comprise the plurality of contact openings.

21. The assembly of claim 20, wherein the second sides of each of the cores further comprises a plurality of recesses, wherein one of the plurality of contact openings appears in each of the recesses.

22. The assembly of claim 21, wherein the recesses are configured to receive feedthrough pins to be welded to contacts accessible through the contact openings in the recesses.

23. The assembly of claim 17, wherein the connector block of each of the cores is affixed to its core by an adhesive.

24. The assembly of claim 17, wherein each of the cores further comprises an alternating series of contacts and seals in its core opening.

25. The assembly of claim 24, wherein the seals are formed of an elastomer material.

26. The assembly of claim 24, wherein the contacts and seals are touching in each of the alternating series.

27. The assembly of claim 26, wherein the contacts and seals are interference fit in each of the core openings.

28. The assembly of claim 27, wherein each core opening ends along its long axis at an edge stop.

29. The assembly of claim 28, wherein each end stop is configured to self-align the contacts with the plurality of contact openings in its core when the alternating series is pushed against the end stop.

30. The assembly of claim 24, further comprising a plurality of feedthrough pins each electrically coupled to one of the contacts accessible through one of the connector openings.

31. The assembly of claim 17, wherein the affixing means in each core is formed in or of the rigid insulative material of which its core is formed.

* * * * *